United States Patent [19]
Shwe et al.

[11] Patent Number: 5,587,525
[45] Date of Patent: * Dec. 24, 1996

[54] FORMATION FLUID FLOW RATE DETERMINATION METHOD AND APPARATUS FOR ELECTRIC WIRELINE FORMATION TESTING TOOLS

[75] Inventors: Than Shwe; John M. Michaels, both of Houston, Tex.

[73] Assignee: Western Atlas International, Inc., Houston, Tex.

[*] Notice: The term of this patent shall not extend beyond the expiration date of Pat. No. 5,473,939.

[21] Appl. No.: 429,722

[22] Filed: Apr. 27, 1995

Related U.S. Application Data

[63] Continuation-in-part of Ser. No. 48,814, Jun. 16, 1993, Pat. No. 5,473,939, which is a continuation-in-part of Ser. No. 903,088, Jun. 19, 1992, abandoned.

[51] Int. Cl.$^6$ ................................................. E21B 47/06
[52] U.S. Cl. ........................ 73/15.52; 73/152.24; 166/264
[58] Field of Search ...................... 73/151, 155, 861.04, 73/152.01, 152.52, 152.51, 152.24; 166/264

[56] References Cited

U.S. PATENT DOCUMENTS

| | | | |
|---|---|---|---|
| 3,035,440 | 5/1962 | Reed | 73/151 |
| 3,277,440 | 10/1966 | Gouilloud et al. | 73/151 |
| 4,043,192 | 8/1977 | Shuck | 73/155 |
| 4,423,625 | 1/1984 | Bostic, III et al. | 73/155 |
| 4,434,653 | 5/1984 | Montgomery | 73/151 |
| 4,507,957 | 4/1985 | Montgomery et al. | 73/151 |
| 4,760,741 | 8/1988 | Koopmans et al. | 73/151 X |
| 4,893,505 | 1/1990 | Mardsen et al. | 73/155 |
| 5,329,811 | 7/1994 | Schultz et al. | 73/155 |
| 5,377,755 | 1/1995 | Michaels et al. | 166/264 |

*Primary Examiner*—Richard Chilcot
*Assistant Examiner*—Paul D. Amrozowicz
*Attorney, Agent, or Firm*—Richard A. Fagin

[57] ABSTRACT

A method of determining the volume of a fluid sample withdrawn from an earth formation penetrated by a wellbore is disclosed. The method includes the step of positioning a formation testing tool adjacent to the earth formation. The tool includes a probe which can be selectively placed in hydraulic communication with the formation and excluded from hydraulic communication with the wellbore. The probe can be in hydraulic communication with a pressure transducer. The tool includes a sample chamber selectively placed in hydraulic communication with the probe. The chamber includes means for measuring the volume of the chamber and means for selectively controlling the volume of the chamber. The method further includes the steps of placing the probe in hydraulic communication with the formation, placing the sample chamber in hydraulic communication with the probe and selectively increasing the volume of the chamber while measuring the volume of the chamber and the pressure, determining the volume of the chamber when a fluid from the wellbore disposed within the probe at the start of withdrawal of the sample ceases to expand, by determining an expansion volume at which the pressure decreases less rapidly with respect to an increase in chamber volume, and determining the volume of the fluid sample by subtracting the expansion volume from a total volume of fluid withdrawn into the sample chamber.

7 Claims, 3 Drawing Sheets

FORMATION FLUID FLOW RATE DETERMINATION METHOD AND APPARATUS FOR ELECTRIC WIRELINE FORMATION TESTING TOOLS

CROSS-REFERENCE TO RELATED APPLICATIONS

The present application is a continuation-in-part of U.S. patent application Ser. No. 08/048,814, filed on Jun. 16, 1993 and entitled "Method and Apparatus for Pressure, Volume and Temperature Measurement and Characterization of Subsurface Formations", now U.S. Pat. No. 5,473,939, which is itself a continuation-in-part of U.S. patent application Ser. No. 07/903,088, filed on Jun. 19, 1992, now abandoned.

BACKGROUND OF THE INVENTION

1. Field of the Invention

The present invention is related to the field of electric wireline tools used to sample fluids contained within pore spaces of earth formations. More specifically, the present invention is related to methods of determining various properties of the earth formation by interpreting pressure readings made by electric wireline formation testing tools.

2. Description of the Related Art

Electric wireline formation testing tools are used to withdraw samples of fluids contained within pore spaces of earth formations and to make measurements of fluid pressures within the earth formation. Calculations made from these measurements can be used to assist in estimating the total fluid content within the earth formation.

Formation testing tools known in the art are typically lowered at one end of an armored electrical cable into a wellbore penetrating the earth formations. The formation testing tool typically comprises a tubular probe which is extended from a tool housing and then is impressed onto the wall of the wellbore. The probe typically is sealed on its outside diameter by an elastomeric packing element to exclude fluids from within the wellbore itself from entering the interior of the probe when fluids are withdrawn from the earth formation through the probe. The probe is selectively placed in hydraulic communication, by means of various valves, with sampling chambers included in the tool. Hydraulic lines which connect the probe to the various sample chambers can include connection to a highly accurate pressure sensor to measure the fluid pressure within the hydraulic lines. Other sensors in the tool can make measurements related to the volume of fluid which has entered some of the sample chambers during a test of a particular earth formation.

One of the properties of the earth formation which can be determined using measurements made by the wireline formation testing tool is permeability. Permeability is determined by, among other methods, calculating a rate at which a fluid having a known viscosity moves through the pore spaces within the formation when a predetermined differential pressure is applied to the formation. As previously stated, the formation testing tool typically includes a sensor to make measurements related to the volume of fluid entering the sample chamber, and further includes a pressure sensor which can be used to determine the fluid pressure in the hydraulic lines connecting the probe to the sample chamber. It is further possible to determine the viscosity of the fluid in the earth formation by laboratory analysis of a sample of the fluid which is recovered from the sample chamber.

In a method known in the art, the flow rate of the fluid from the formation into the sample chamber is typically determined by measuring the amount of time taken to fill the sample chamber, and calculating a flow rate by dividing the chamber volume by the measured time. The flow rate thus calculated can be used to calculate the permeability.

A drawback to the method known in the art for determining permeability from measurements made by the wireline formation test tool is that the test tools known in the art do not measure the sample chamber volume with sufficient accuracy and resolution in order to be able to determine that the flow rate calculated is representative of fluid flow only of the native fluid within the formation. To make measurements related to the volume of the sample chamber, the formation testing tools known in the art typically include means such as a direct-current "stepper" motor coupled to a screw drive, which moves a piston bounding one end of the sample chamber. It is typically not possible to control the volume change or the volume change rate caused by each one of the motor "steps". The testing tools known in the art include means for inferring the chamber volume by counting the number of motor steps, but by only counting steps, the testing tools known in the art can only indirectly determine the volume of the sample chamber. The volume of the chamber may therefore not be precisely known at any instant in time between the initiation of drawing a sample and the conclusion of drawing the sample. Subtle changes in the relationship of sample pressure to sample volume, which can be important in determining the permeability of the formation, can be obscured by the relatively low resolution of the test chamber volume measurement of the formation test tools known in the art. Subtle changes in the pressure/volume relationship of the sample can be affected by, among other things, the composition of the fluid actually withdrawn from the pore spaces of the formation.

Permeability which is calculated from measurements made of the pressure and the volume of the fluid being drawn into the chamber during the withdrawal of a sample can be affected by the composition of the fluid which is actually drawn into the chamber during draught of the sample. For example, when a wellbore is drilled through the earth formations, it is typically filled with a fluid having a specific gravity large enough so the fluid can exert hydrostatic pressure against the earth formation which can restrain native fluids within the formation from entering the wellbore. It is even more typical for the hydrostatic pressure of the fluid in the wellbore to at least slightly exceed the fluid pressure in the formation, so a part of the fluid within the wellbore, called "mud filtrate", typically is forced into the pore space in the formation by differential pressure. In addition, when the probe is first hydraulically connected to the sample chamber, it is still substantially filled with the fluid from within the wellbore, called "drilling mud". Both the drilling mud and the mud filtrate can have compressibilities and viscosities which are different from the fluid in the formation. Because the fluid which is actually drawn into the sample chamber will probably contain at least some drilling mud and mud filtrate, a formation permeability determination based only on the time taken for the sampled fluid to fill the volume of the sample chamber therefore can be erroneous because the flow rate thus determined can be in error.

The drawback to the formation test tools known in the art as described herein can be better understood by referring to FIGS. 1A and 1B. FIG. 1A is a graphic representation of fluid pressure with respect to time shown as curve 210, and is a graphic representation of volume with respect to time shown as curve 212. When a sample is first drawn, as shown beginning on curve 210 at a point indicated by reference numeral 214, the volume of the test chamber is increased. Some of the increase in chamber volume is dissipated by reducing the pressure of fluid in the hydraulic lines so that the hydraulic line pressure balances the pressure of the fluid in the formation, as indicated at the point shown at reference numeral 216. As the sample chamber volume increases further, the chamber pressure drops below the formation pressure and flow from the formation into the chamber begins. However, some of the fluid in the formation near the probe can be the "mud filtrate" previously described herein. The mud filtrate can have different compressibility and viscosity than does the native fluid in the formation. Consequently, the relationship of chamber pressure to chamber volume can be different when the fluid being drawn into the chamber consists of mud filtrate, as can be observed on curve 210 between points indicated with reference numerals 216 and 218. After the pressure drop in the formation caused by the increasing chamber volume is finally communicated to the fluid in the formation, as indicated on curve 210 at the point having numeral 218, the fluid movement into the chamber with respect to increasing chamber volume is affected principally by the properties of the fluid in the formation, as indicated between points 218 and 220 on curve 210. At point 220, the chamber has been expanded to a predetermined maximum volume, and the pressure in the chamber begins to increase as formation fluid continues to flow into the chamber. The flow will continue until the chamber pressure equals the formation pressure.

FIG. 1B shows the relationship of chamber pressure with respect to chamber volume. Curve 222 is a graphic representation of the relationship of pressure to volume for the sample test shown as related to time in FIG. 1A. For example, the previously referred to expansion of drilling mud in the probe and hydraulic line is shown between points 224 and 226; the expansion of the mud filtrate in the formation pore spaces is shown between points 226 and 228; and the portion of the chamber volume being filled by native fluid flow in the formation is shown between points 228 and 230.

The formation testing tools known typically do not have means for determining the volume of the chamber at intermediate points, such as 226 and 228 in curve 222 in FIG. 1B, to a sufficient degree of precision to determine the amount of flow corresponding only to the formation fluid.

Accordingly it is an object of the present invention to provide a formation test tool having a means for resolving the volume of the test chamber to a sufficient degree of accuracy to enable determining whether the fluid flowing into the formation test tool is caused by fluid movement from the pore space of the formation.

It is a further object of the present invention to provide a method of calculating permeability of the hydraulic zone by measuring the flow rate of fluid into a sample chamber of a wireline formation test tool after determining that the fluid flowing into the test chamber is caused to flow by movement of formation fluid in the pore space of the formation.

SUMMARY OF THE INVENTION

The present invention is a method of determining the volume of a fluid sample withdrawn from an earth formation penetrated by a wellbore. The method includes the step of positioning a formation testing tool adjacent to the earth formation. The testing tool includes a tubular probe which can be selectively placed in hydraulic communication with said the formation and excluded from hydraulic communication with the wellbore. The tool also includes a sample chamber selectively placed in hydraulic communication with the probe. The chamber includes means for measuring the volume of the chamber and has means for selectively controlling the volume of the chamber. The tool further includes a pressure transducer in hydraulic communication with the probe.

The method further includes the steps of placing the probe in hydraulic communication with the earth formation, placing the sample chamber in hydraulic communication with the probe and selectively increasing the volume of the chamber while measuring the volume of the chamber and the pressure, determining the volume of the chamber when a fluid from the wellbore, which is disposed within the probe at the start of withdrawal of the fluid sample ceases to expand by determining an expansion volume at which the measured pressure decreases less rapidly with respect to an increase in the chamber volume, and determining the volume of the fluid sample by subtracting the aforementioned expansion volume from a total volume of fluid withdrawn into the sample chamber.

In a particular embodiment of the invention, a flow rate of fluid withdrawn from the earth formation can be determined by measuring the amount of time elapsed between the end of the expansion of the wellbore fluid in the probe and the withdrawal of the volume of the sample.

DESCRIPTION OF THE PREFERRED EMBODIMENT

Figure 2:
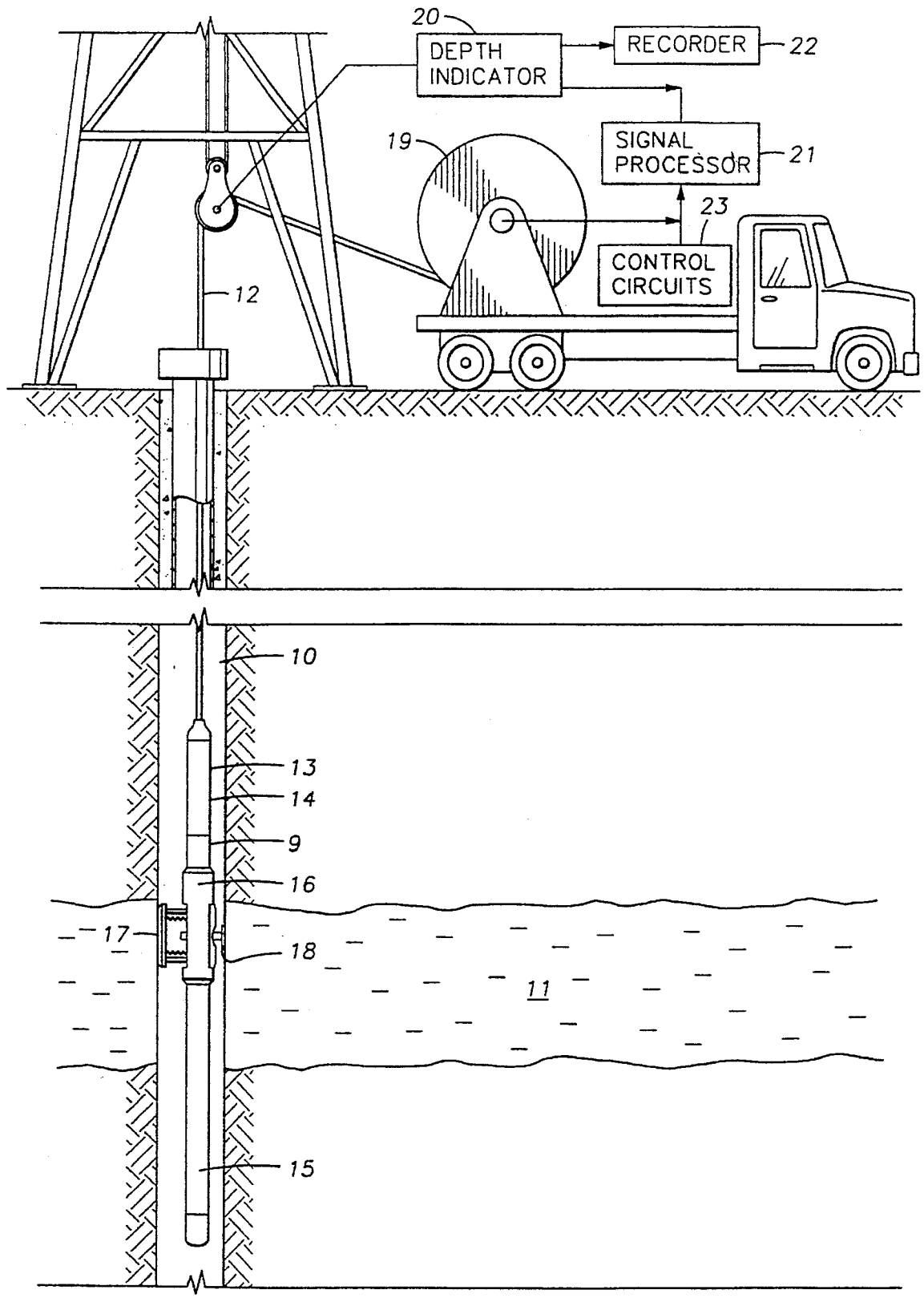
FIG. 2 shows a formation test tool according to the present invention disposed within a wellbore.

A wireline formation test tool is generally shown in FIG. 2 at 13. The tool 13 is attached to one end of an armored electrical cable 12 and is lowered into a wellbore 10 drilled through the earth. The cable 12 is extended into the wellbore 10 by means of a winch 19 located at the earth's surface.

The tool 13 comprises a back-up shoe and mechanism for extending the shoe, shown generally at 17, which are disposed within a housing 16. The housing 16 also contains a tubular probe 18 which can be selectively extended and put into contact with the wall of the wellbore 10, as will be further explained. A sample tank 15 can be attached to the lower end of the housing 16 and can be selectively hydraulically connected to the probe 18 in order to store samples of fluids withdrawn from the earth. The probe 18, the back-up shoe 17 and selective valves (not shown) disposed within the housing 16 for operating the probe 18 and the shoe 17 receive hydraulic operating power from an hydraulic power unit 9 attached to the upper end of the housing 16.

The various functions of the tool 13, including extension of the shoe 17 and extension of the probe 18, can be controlled by the system operator entering command signals into control circuits 23 which are located at the earth's surface and are electrically connected to the cable 12. The command signals are decoded in an electronics unit 14 disposed within the housing 16. As will be further explained, the tool 13 comprises sensors (not shown) for measuring pressure and volume within hydraulic lines (not shown in FIG. 2) connected to a sample chamber (not shown in FIG. 2). Measurements made by the sensors (not shown) are transmitted to the earth's surface as electrical signals by the electronics unit 14. At the earth's surface the signals are decoded by a signal processor 21 which is also electrically connected to the cable 12. The decoded signals are reformatted into measurements which can be observed by the system operator and can be recorded by a recorder 22 connected to the signal processor 21.

As the tool 13 is lowered into the wellbore 10, the depth at which the tool is located is indicated by a depth indicator 20 which is in contact with the cable 12. When the tool 13 is determined to be positioned adjacent to a formation of interest, shown generally at 11, the system operator enters commands into the control circuits 23 to lock the tool 13 in position by extending the back-up shoe 17. The probe 18 is then extended, and withdrawal of a sample can then be initiated.

Figure 3:
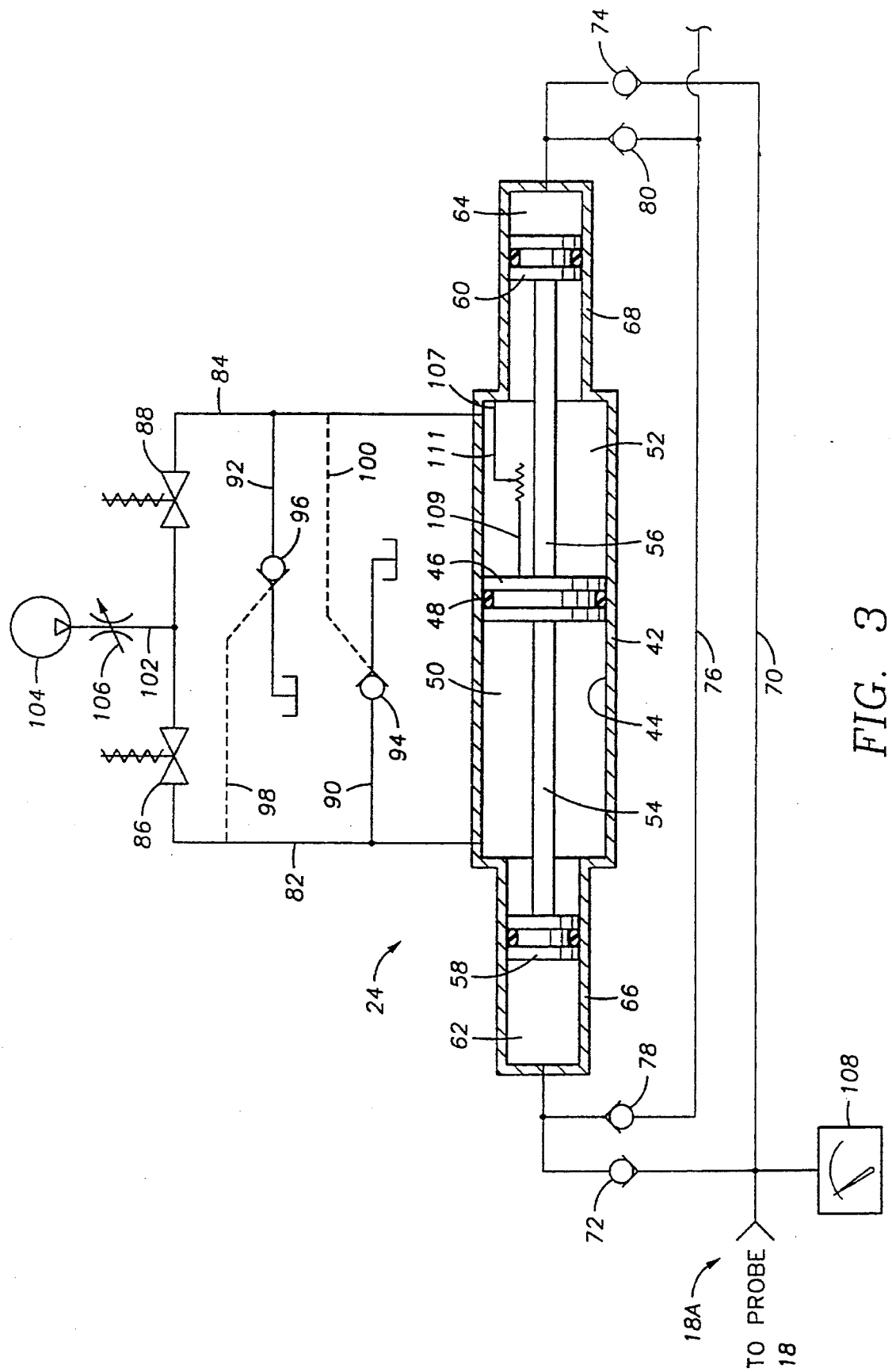
FIG. 3 shows a sampling pump according to the present invention which has a precise measuring apparatus for the pumping chambers.

The means by which a sample can be withdrawn from the formation of interest 11 can be better understood by referring to FIG. 3. A bi-directional, hydraulically powered pump, shown generally at 24, can be used to controllably withdraw fluids through the probe (shown as 18 in FIG. 2), and if so desired by the system operator, the pump 24 can further be used to discharge the fluids into the sample tank (shown as 15 in FIG. 2).

The pump 24 comprises a drive cylinder 44, inside which is located a drive piston 46. The drive piston 46 is sealed against the inner wall of the drive cylinder 44 by an o-ring 48 or similar sealing device. The drive piston 46 is connected on one side to a first drive link 54, and on the other side is connected to a second drive link 56. The first drive link 54 is connected to one side of a first pumping piston 58. The second drive link 56 is similarly connected to a second pumping piston 60 disposed on the opposite side of the drive piston 46 to the first pumping piston 58. The first 58 and the second 60 pumping pistons are each respectively positioned within first 66 and second 68 pump cylinders disposed on opposite ends of the drive cylinder 44. Axial motion of the drive piston 46 is translated into equivalent axial motion of both the first 58 and second 60 pumping pistons, the significance of which will be further explained.

The drive piston 46 is moved by selective application of hydraulic pressure to either one side or to the other side of the drive piston 46. Hydraulic pressure is provided by an hydraulic pump 104 which is disposed in the hydraulic power unit (shown in FIG. 2 as 9). The hydraulic pump 104 is connected to a controllable pressure regulator 106 which provides the hydraulic pressure to move the drive piston 46. The discharge pressure from the regulator 106 can be controlled by the system operator entering appropriate commands into the control circuits (shown in FIG. 1 as 23). The controllable regulator discharge provides the system operator with a substantial degree of control over the rate at which the drive piston 46 moves since as will be further explained the drive piston 46 must overcome forces of fluid pressures acting on the pumping pistons 58, 60 in order to move.

The discharge from the regulator 106 is provided to hydraulic lines 102. The lines 102 connect to a first 86 and to a second 88 selective hydraulic valve. The selective valves 86, 88 can be operated by control signals sent from the control circuits (shown as 23 in FIG. 2) and decoded in the electronics unit (shown at 14 in FIG. 2). The control signals provide operation of the valves 86, 88 in accordance with the pump 24 function selected by the system operator by entering appropriate commands into the control circuits 23, as will be further explained.

When the first valve 86 is opened, hydraulic pressure is applied through a first hydraulic control line 82 to a first chamber 50 in the drive cylinder 44, which is bounded at one end by the drive piston 46 and at the other end by the first pumping piston 58. The diameters of the first pump cylinder 66, and therefore, the first pumping piston 58 are smaller than the diameter of the drive piston 46. Hydraulic pressure within the first drive chamber 50 therefore exerts more force on the drive piston 46 than on the first pumping piston 58, which causes motion of the drive piston 46, and all the previously described components that are attached to it, in the direction of the second pump cylinder 68. Hydraulic oil (not shown) is also present in a second drive chamber 52 disposed on the opposite side of the drive piston 46 and axially bounded by the drive piston 46 on one end and the second pumping piston 60 on the other end. As the drive piston 46 moves toward the second pump cylinder 68, the hydraulic oil in the second drive chamber 52 is displaced through a second hydraulic line 84 into a second discharge line 92 connected to a hydraulic oil supply tank (not shown) through a pilot operated check valve 96. The check valve 96 is held open by the operating hydraulic pressure from the line 102 applied through a control line 98 connected to the first hydraulic line 82. A similar, oppositely connected check valve, shown at 94, is connected through a control line 100 to the second hydraulic line 84, and as will be explained, vents the first hydraulic line 82 to the supply tank (not shown) when the drive piston 46 is moved in the opposite direction.

Motion of the drive piston 46 can be reversed by closing the first valve 86 and opening the second valve 88, thereby applying hydraulic pressure through the second hydraulic line 84 to the second drive chamber 52. The operation of the two valves 86, 88 can be performed automatically if the system operator instructs the control circuits 23 to operate the pump 24 continuously. The second pumping piston 60 can be substantially the same diameter as the first pumping piston 58, and thereby be smaller in diameter than the drive piston 46. Therefore hydraulic pressure applied to the second drive chamber 52 will cause motion of the drive piston 46 towards the first pump cylinder 66. As previously explained, the pressure on the second line 84 is also conducted through the control line 100 to open the pilot operated check valve at 94, which enables venting of the first drive chamber 50 to the supply tank (not shown).

Axial motion of the drive piston 46, which as previously explained is translated into equivalent axial motion of the first 58 and second 60 pumping pistons, results in corresponding changes in volume of a first 62 and second 64 pump chamber. The pump chambers 62, 64 can be selectively hydraulically connected to the probe 18 in order to withdraw fluid from the formation, as will be further explained.

A particular feature of the present invention which enables direct determination of the volume of the first 62 and the second 64 pump chambers is a displacement sensor, which in the present embodiment can be a linear potentiometer 111 disposed inside the drive cylinder 44 and connected by a link 109 to the drive piston 46. Axial motion of the drive piston 46 results in directly corresponding change in the resistance of the potentiometer 111 as applied to a signal line 107. The resistance as applied to the signal line 107 is converted into a corresponding signal in the electronics unit (shown in FIG. 2 as 14), which signal can be decoded in the signal processor (shown as 21 in FIG. 2) and converted into a measurement of the position of the drive piston 46, and thereby the exact volume of either pump chamber 62, 64, since the axial motion of all three pistons 46, 58, 60 is equivalent. It is contemplated that other means for measuring the axial position (and thereby the volume of the pumping chambers 62, 64) of the drive piston 46 or of the first 58 or second 60 piston can be employed, for example an acoustic travel time sensor disposed within either drive chamber 50 or 52. The linear potentiometer 111 of the present invention is used only as a matter of convenience and should not be construed as an explicit limitation on the means for determining the volume of the pumping chambers 62, 64.

Another advantageous feature of the present invention is that the rate of movement of the drive piston 46 can be controlled by the system operator. As previously explained, the drive piston 46 must exert force sufficient to overcome opposing force caused by the formation (shown as 11 in FIG. 2) fluid pressure in the pumping chambers 62, 64 acting on their respective pumping pistons 58, 60 in order to move. The amount of hydraulic pressure applied to the drive piston 46 is controllable by the system operator through the regulator 106. It is therefore possible to operate the drive piston 46 at an hydraulic pressure which just overcomes the formation fluid pressures acting on the pumping pistons 58, 60, in which case the drive piston 46 wild move extremely slowly. Moving the drive piston 46 very slowly reduces the possibility, among others, that subtle changes in a relationship between the volume of the pumping chambers 62, 64 and the fluid pressure will go undetected.

When withdrawal of a sample from the formation (shown at 11 in FIG. 2) is begun, the drive piston 46 is typically positioned so that either the first 58 or the second 60 pumping piston is fully extended into its respective pumping chamber 62 or 64. Withdrawal of a sample is begun by application of hydraulic pressure to the appropriate drive chamber 50 or 52 (adjacent to the completely compressed pump chamber into which its pump piston 58 or 60 is fully extended), whereupon the drive piston 46 moves and correspondingly displaces the pumping pistons 58, 60, thereby increasing the volume of the fully compressed pumping chamber 62 or 64.

The first 62 and second 64 pumping chambers are connected, respectively to a first 72 and a second 74 inlet check valve, both of which enable flow from the probe (shown as 18 in FIG. 2) into an inlet flowline 70 (connected as shown at 18A to the probe 18) on the expansion stroke of the respective pumping chamber 62 or 64. The inlet flowline 70 is further connected to a precision pressure transducer 108 (which is itself connected to the electronics unit 14) which enables substantially continuous measurement of the pressure in the flowline 70. The use of the pressure measurement made by the transducer 108 in the present invention will be further explained.

During the compression stroke corresponding to expansion of the opposing chamber 64 or 62, discharge from the first 62 or from the second 64 chamber is conducted, respectively, through a first 78 or second 80 discharge check valve to a discharge line 76. The discharge line 76 can be selectively hydraulically connected to the sample tank (shown in FIG. 2 as 15) or to the wellbore (shown in FIG. 2 as 10). Suitable hydraulic valving for selectively hydraulically connecting the discharge line 76 to the sample tank 15 or to the wellbore 10 is well known in the art. A typical example of this type of valve arrangement is described in U.S. Pat. No. 5,377,755 issued to Michaels et al and assigned to the assignee of the present invention. The selective valving is shown in FIG. 6 of the Michaels et al '755 patent as solenoid valves 189, 200, 202, 204, 206, 216, 226, 228, 230, 232 and 234. If the system operator desires, for example, to fill the sample tank 15 with fluid withdrawn through the probe 18, pumping can be continued by automatic selective operation of the valves 86, 88 by the control circuits 23, as previously described herein.

Figure 1A:
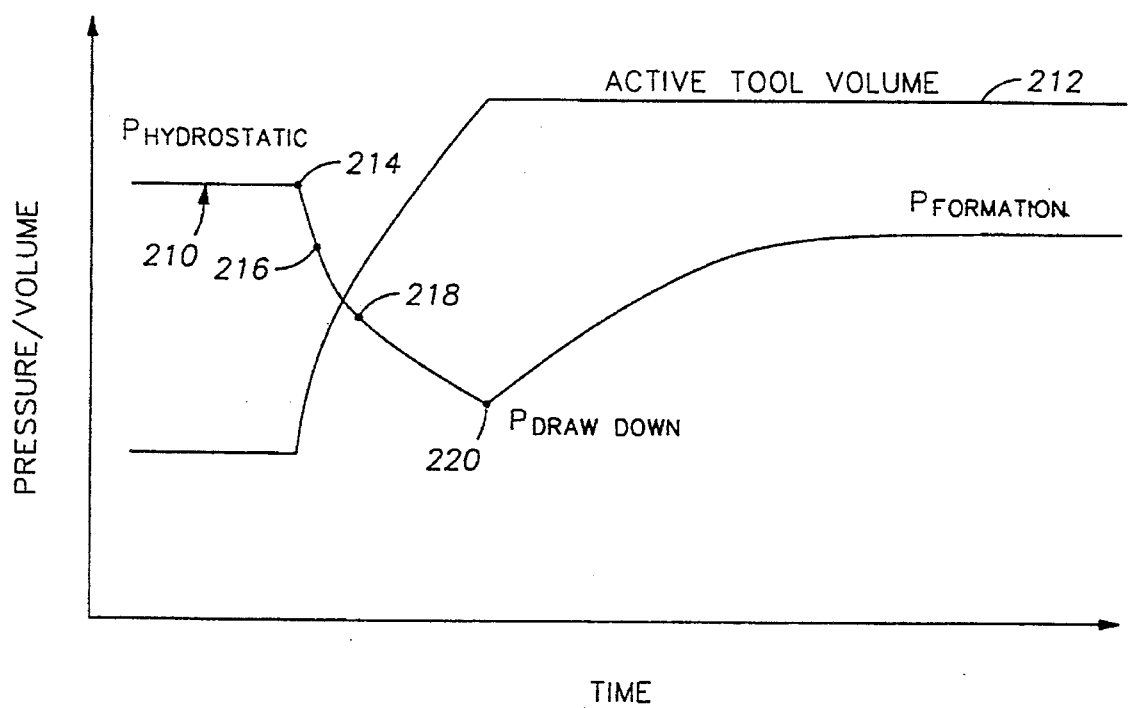
FIG. 1A shows a graph of sample pressure with respect to time as measured by a formation testing tool.
Figure 1B:
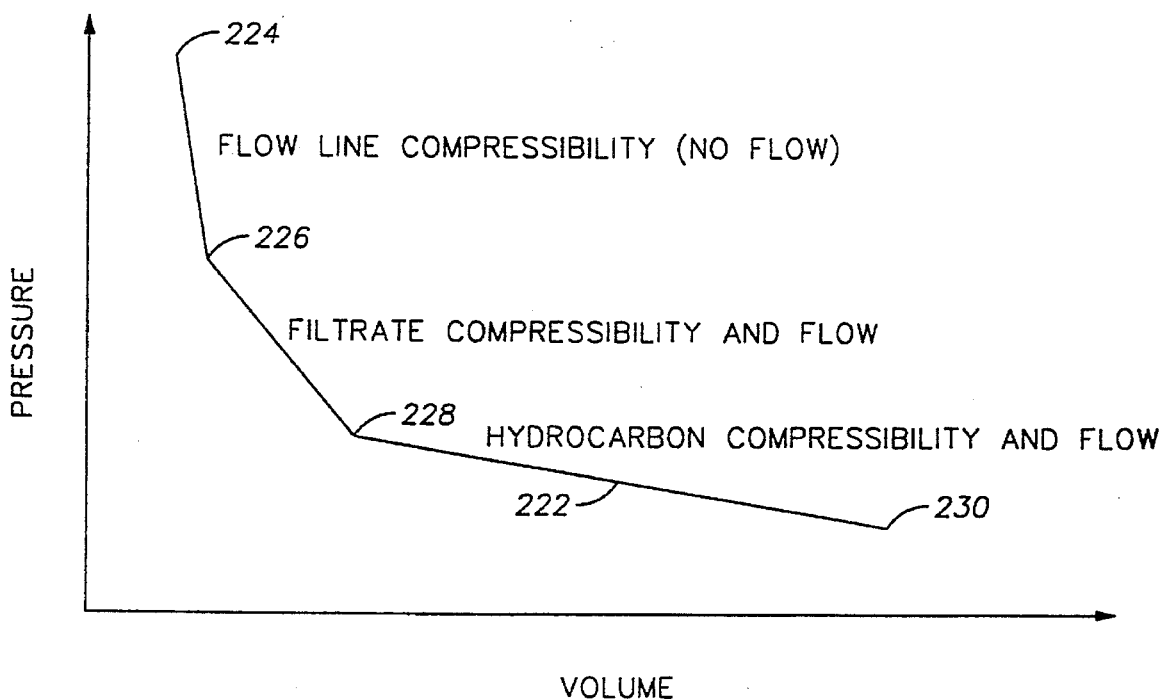
FIG. 1B shows a graph of sample volume with respect to pressure corresponding to the time-based graph of FIG. 1A.

Referring to FIGS. 1A and 1B, the improvement provided by the present invention in determining permeability of the formation (shown as 11 in FIG. 2) will be better understood. FIG. 1A is a graphic representation of pressure as measured by the transducer (shown in FIG. 3 as 108) with respect to time, shown generally as curve 210. A corresponding curve 212 represents the approximate volume of the pumping chamber (either 62 or 64 in FIG. 3) with respect to time as the chamber is expanded. The beginning of the sample withdrawal is indicated at point 214. During chamber expansion the pressure drop occurring between points 214 and 216 on curve 210 is related to decompression of fluid from the wellbore (shown as 10 in FIG. 2) which is present in the probe (shown as 18 in FIG. 3) and the intake flowline (shown as 70 in FIG. 3). Further pressure drop from points 216 to 218 can be representative of expansion of "mud filtrate" which may have been displaced by hydrostatic pressure into the pore space of the formation (shown as 11 in FIG. 2), as is understood by those skilled in the art. Still further pressure drop from points 218 to 220 can be representative of decompression and subsequent flow of native fluid withdrawn from the formation 11. The native fluid can include oil and/or natural gas.

The rate of pressure drop in the flowline (shown as 70 in FIG. 3) and chamber (shown as 62 or 64 in FIG. 3), indicated by the slope of curve 210 during chamber expansion generally between points 214 and 220, can be affected by the bulk compressibility of the fluid which is being drawn into the probe (shown as 18 in FIG. 2), flowline and chamber. Bulk compressibility is a property which is specific to individual compositions of fluid, as is understood by those skilled in the art. Identification of the compressibility and consequently the nature of the fluid drawn into the probe, requires determining the relationship between pressure and volume of the fluid under investigation. As can be observed by referring to FIG. 1B, which is a graphic representation of measured pressure with respect to chamber volume, points corresponding to the expansion of different types of fluid (shown for example as points 216 and 218 in FIG. 1A) can be indicated as occurring at specific chamber volumes. The present invention, which includes the linear potentiometer (shown as 111 in FIG. 3), provides a substantially direct measurement of the volume of the chamber, whereby pressure drop measurements made between points such as 226 and 228 on curve 222 in FIG. 1B (corresponding respectively to points 216 and 218 in FIG. 1A) can be used to determine the different compressibilities of the various fluids drawn into the chamber, because the volume of the chamber is always precisely determinable.

By identifying the precise volume of native fluid withdrawn from the formation (shown as 11 in FIG. 2), as can be generally seen between points 228 and 230 in FIG. 1B, it is then possible to make a more precise calculation of the flow rate of the native fluid into the chamber with respect to pressure drop. As is understood by those skilled in the art, determination of native fluid flow rate with respect to pressure drop can enable estimation of permeability of the formation 11.

Other embodiments providing the improvement over the prior art as described in the present invention will be readily devised by those skilled in the art. The description of the invention provided herein is to be used only as an example and not as a limitation on the scope of the invention. The scope of the invention should only be limited only by the claims appended hereto.

What is claimed is:

1. An apparatus for withdrawing a fluid sample from an earth formation penetrated by a wellbore, comprising:

an elongated housing adapted to traverse said wellbore;

a probe disposed within said housing and adapted to be selectively placed in contact with said earth formation;

a pumping chamber disposed within said housing and selectively placed in hydraulic communication with said probe, said pumping chamber having a selectively controllable volume;

a pressure transducer disposed within said housing and in hydraulic communication with said probe;

means for selectively increasing and selectively decreasing said volume of said pumping chamber;

means for measuring said volume of said pumping chamber; and means for recording measurements of said volume of said pumping chamber and pressure measurements made by said transducer with respect to time so that a measurement of a volume of fluid withdrawn through said probe into said pumping chamber can be determined exclusive of an expansion volume of fluid from said wellbore disposed within said probe prior to initiation of withdrawal of said fluid sample.

2. The apparatus as defined in claim 1 wherein said pumping chamber comprises a bi-directional pump having pumping chambers disposed on either end, said pumping chambers selectively placed in hydraulic communication with said probe, said pumping chambers further comprising means for determining an axial position of pumping pistons adapted to travel axially through said pumping chambers for displacing fluid through said pumping chambers.

3. The apparatus as defined in claim 2 further comprising an electronics unit including a signal transmitter for sending signals generated by said means for determining axial position and by said pressure transducer to recording equipment disposed at the earth' surface.

4. The apparatus as defined in claim 1 further comprising a sample tank attached to said housing and selectively placed in hydraulic communication with said probe for collecting and transporting said fluid sample.

5. A method of determining the volume of a fluid sample withdrawn from an earth formation penetrated by a wellbore, comprising:

positioning a formation testing tool adjacent to said earth formation, said tool including a probe selectively operable to be in contact with said earth formation, said tool including a pumping chamber having means for continuously measuring the volume of said pumping chamber, said pumping chamber having means for selectively placing said pumping chamber in hydraulic communication with said probe, said pumping chamber having selectively operable means for controlling said volume, said tool including a pressure transducer in hydraulic communication with said probe;

placing said probe in hydraulic communication with said earth formation;

placing said pumping chamber in hydraulic communication with said probe and selectively increasing said volume of said pumping chamber;

measuring fluid pressure in said probe by means of said transducer and simultaneously measuring said volume of said pumping chamber;

determining said volume of said pumping chamber when a fluid from said wellbore disposed within said probe at the start of withdrawal of said fluid sample ceases to expand by determining an expansion volume at which said fluid pressure decreases at a different rate with respect to an increase in said volume of said pumping chamber; and determining said volume of said fluid sample by subtracting said expansion volume from a total volume of fluid withdrawn into said pumping chamber.

6. The method as defined in claim 5 further comprising the step of determining a flow rate of fluid from said earth formation into said pumping chamber by measuring a time elapsed between cessation of expansion of said fluid from said wellbore and withdrawal of said volume of said fluid sample.

7. The method as defined in claim 6 further comprising determining said volume of said fluid sample and said flow rate by determining a second volume at which a mud filtrate disposed within said earth formation ceases to expand and subtracting said second volume from said volume of said fluid sample.

* * * * *